US00RE39874E

(19) United States
(12) Reissued Patent
Berge et al.

(10) Patent Number: US RE39,874 E
(45) Date of Reissued Patent: Oct. 9, 2007

(54) LENS WITH VARIABLE FOCUS

(75) Inventors: Bruno Berge, Lyons (FR); Jérôme Peseux, Solaize (FR)

(73) Assignee: Varioptic, Lyons (FR)

(21) Appl. No.: 10/819,888

(22) PCT Filed: Oct. 7, 1998

(86) PCT No.: PCT/FR98/02143

§ 371 (c)(1),
(2), (4) Date: Jul. 25, 2000

(87) PCT Pub. No.: WO99/18456

PCT Pub. Date: Apr. 15, 1999

Related U.S. Patent Documents

Reissue of:
(64) Patent No.: 6,369,954
Issued: Apr. 9, 2002
Appl. No.: 09/529,193
Filed: Jul. 25, 2000

(30) Foreign Application Priority Data

Oct. 8, 1997 (FR) ..... 97 12781

(51) Int. Cl.
*G02B 1/06* (2006.01)
*G02B 3/12* (2006.01)
*G02B 26/00* (2006.01)
*G02F 1/13* (2006.01)

(52) U.S. Cl. ..... 359/666; 359/665; 359/291; 349/200

(58) Field of Classification Search ..... 349/57, 349/200; 359/290, 291, 665, 666
See application file for complete search history.

(56) References Cited

U.S. PATENT DOCUMENTS 4,030,813 A * 6/1977 Kohashi et al. ..... 345/84
5,659,330 A * 8/1997 Sheridon ..... 359/245
6,449,081 B1 * 9/2002 Onuki et al. ..... 359/245
6,702,483 B2 * 3/2004 Tsuboi et al. ..... 396/449
2005/0002113 A1 * 1/2005 Berge ..... 359/666
2006/0126190 A1 * 6/2006 Berge et al. ..... 359/665
2006/0152814 A1 * 7/2006 Peseux ..... 359/665
2007/0002455 A1 * 1/2007 Berge et al. ..... 359/665

FOREIGN PATENT DOCUMENTS

FR 822 886 A * 1/1937
JP 2001-013306 A * 1/2001

OTHER PUBLICATIONS

"Mechanically Assisted Liquid Zoom Lens System", F.C. Wippermann, P. Schreiber, A. Brauer and B. Berge; Novel Optical Systems Design and Optimization IX; Proceedings of SPIE vol. 6289 (2006) pp. 62890T 1–9.*
"Liquid Lens Based on Electrowetting", J. Crassous, C. Gabay, G. Liogier and B. Berge; Adaptive Optics and Applications III; Proceedings of SPIE vol. 5639 (2004) pp. 143–148.*
"Variable Focus Liquid Lens for Portable Applications", S. Kuiper, B.H.W. Hendricks, L.J. Huijbregrts, a. Hirschberg, C. A. Renders and M.A.J. vanAs; Current Developments in Lens Design and Optical Engineering V; Proceedings of SPIE vol. 5523 (2004) pp. 100–109.*

(Continued)

*Primary Examiner*—David N. Spector
(74) *Attorney, Agent, or Firm*—Foley & Lardner LLP

(57) ABSTRACT

A variable focus lens comprising a chamber (12) filled with a first liquid (13), a drop of a second liquid (11) being disposed at rest on a region of a first surface of an insulating wall of the chamber, the first and second liquids being non miscible, of different optical indexes and of substantially same density. The first liquid is conductive and the second liquid is insulating. The lens further comprises means for applying a voltage between the conductor liquid and an electrode (16) placed on the second surface of said wall; and centering means for maintaining the centering of the edge of the drop while the voltage is applied and for controlling the shape thereof.

59 Claims, 3 Drawing Sheets

OTHER PUBLICATIONS

Sheridon, N.K.; Electrocapillary Imaging Devices for Display and Data Storage; Xerox Disclosure Journal; vol. 4, No. 3 May 1979, pp. 385 and 386.*

Berge, B; Electrocapillarite et mouillage de films isolants par l'eau; Comptes Rendus Des Seances De L'Academie Des Sciences, vol. 317, No. 2, Jun. 22, 1993; pp. 157–163.*

* cited by examiner

LENS WITH VARIABLE FOCUS

Matter enclosed in heavy brackets [ ] appears in the original patent but forms no part of this reissue specification; matter printed in italics indicates the additions made by reissue.

BACKGROUND OF THE INVENTION (1) Field of the Invention

The present invention relates to the field of variable focal lenses, and more specifically to liquid lenses having a variable electrically controlled focus.

(2) Description of Related Art

An article of B. Berge entitled "Electrocapillarité et mouillage de films isolants per l'eau" published in 1993 in C.R. Acad. Sci. Paris, t. 317, serial II, pages 157 to 163, discloses a device comprising a drop of conductor liquid placed on a dielectric film covering a flat electrode. A voltage may be applied between the liquid conductor drop and the electrode. This article describes a theoretical study of the wetting variation of a dielectric material with respect to a conductor liquid and shows that the wetting increases substantially in presence of an electric field caused by the voltage existing between the conductor liquid and the electrode. This phenomenon is called electrowetting by the author.

U.S. Pat. No. 5,659,330 discloses a display device using the electrowetting phenomenon to vary the shape of a drop of opaque conductor liquid placed on a dielectric. This document does not suggest the use as an optic lens.

An article of Vallet, Berge and Vovelle, "Electrowetting of water and aqueous solutions on poly(ethylene terephthalate) insulating films", published in Polymer, Vol. 37, N° 12, pages 2465 to 2470, 1996, discloses a deformation of a liquid conductor drop to which a voltage is applied. It is indicated that, when the applied voltage becomes too high, the surface of the drop becomes unstable, and microdroplets may be ejected at the periphery of the drop.

BRIEF SUMMARY OF THE INVENTION

This makes prior art systems inadequate for forming variable lenses. Moreover, these systems need a transparent biasing electrode and a connection for the electrode, which makes the system difficult to manufacture or inefficient.

An object of the present invention is to provide a lens whose focus may vary continuously as a function of an electric control, by using the phenomenon of electrowetting.

Another object of the present invention is to provide a lens which is simple to manufacture.

Another object of the present invention is to provide a lens which is simple to use.

For achieving these objects, the present invention provides a variable focus lens comprising a chamber filled with a first liquid, a drop of a second liquid being disposed at rest on a region of a first surface of an insulating wall of the chamber, the first and second liquids being non miscible, of different optical indexes and of substantially same density. The first liquid is conductive and the second liquid is insulating. The lens further comprises means for applying a voltage between the conductor liquid and an electrode placed on the second surface of said wall; and centering means for maintaining the centering of the edge of the drop while the voltage is applied and for controlling the shape thereof.

According to an embodiment of the invention, the centering means allows a continuous maintaining of the centering of the drop and a continuous control of the shape of the edge of the drop while a varying voltage is applied by said means for applying a voltage.

According to an embodiment of the invention, the first surface is substantially flat, the contact region is circular and centered about an axis which is perpendicular to the first surface.

According to an embodiment of the invention, the centering means corresponds to a progressive thickening of the second surface of the wall of the chamber towards said axis, said electrode being applied against said second surface.

According to an embodiment of the invention, the centering means corresponds to a radial decrease of the wetting with respect to the first liquid, towards the center of said contact region with the second liquid.

According to an embodiment of the invention, the centering means corresponds to a radial gradient of the dielectric constant of said wall of the chamber at the level of said contact region with the second liquid.

According to an embodiment of the invention, the first surface is substantially flat, the contact region 15 is circular and centered about an axis perpendicular to the first surface, and the centering means comprises an electrode formed of one or several circular concentric strips insulated from each other, centered about said axis, the circular strips being supplied by distinct voltage sources of values decreasing towards said axis.

According to an embodiment of the invention, the chamber is cylindrical, the first surface is the internal surface of the chamber, the contact region with the second liquid corresponds to a cylindrical section of the chamber, the centering means is comprised of one or several cylindrical electrodes of same diameter, insulated from each other, placed side by side against the external surface of the chamber at the level of the border of said contact region, the electrodes being supplied by different voltages of values decreasing towards the center of said contact region.

According to an embodiment of the invention, the first surface is substantially flat, the contact region is rectangular and symmetric with respect to an axis perpendicular to the first surface and the centering means is comprised of an electrode formed of one or several rectangular concentric strips insulated from each other, symmetric with respect to said axis, the rectangular strips being supplied by distinct voltage sources of decreasing values towards said axis.

According to an embodiment of the invention, said wall is comprised of two non parallel planes and in which said region bridges said two planes.

BRIEF DESCRIPTION OF THE SEVERAL VIEWS OF THE DRAWINGS

The foregoing and other objects, features, aspects and advantages of the invention will become apparent from the following detailed description of embodiments, given by way of illustration and not of limitation with reference to the accompanying drawings.

DETAILED DESCRIPTION OF THE INVENTION

Figure 1:
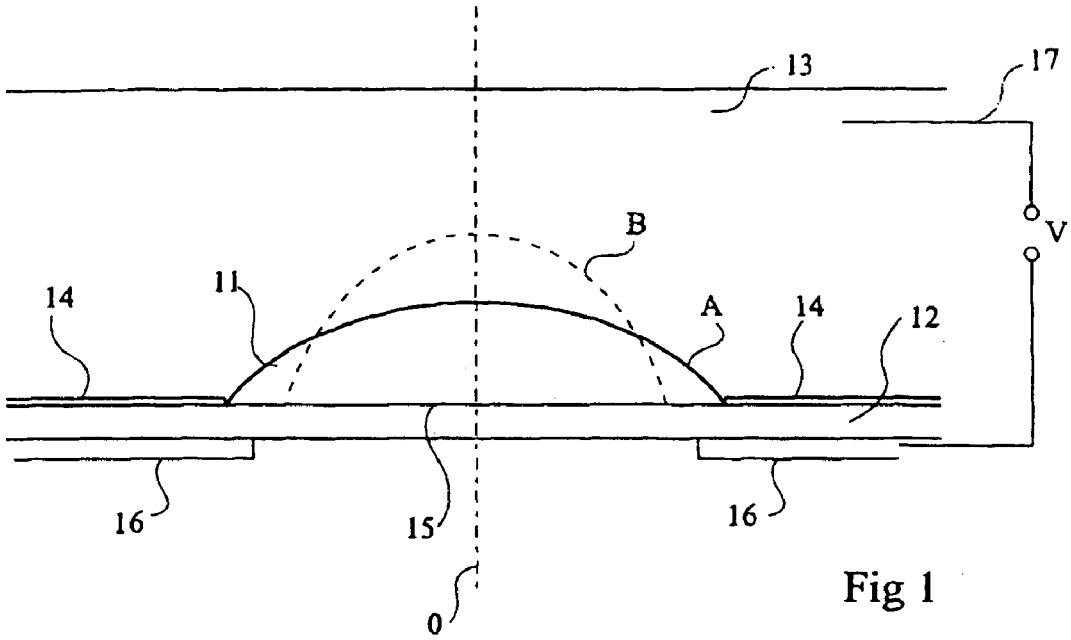
FIG. 1 shows a first embodiment of a variable focus lens according to the present invention.

FIG. 1 shows a simplified cross-section view of a variable focus liquid lens according to a first embodiment of the present invention. A drop of an insulating liquid 11 is located on the internal surface of a wall of a dielectric chamber 12 filled with a conductor liquid 13. The insulating liquid 11 and the conductor liquid 13 are both transparent, not miscible, have different optical indexes and have substantially the same density. The dielectric 12 naturally has a low wetting with respect to the conductor liquid 13. A surface treatment 14 insuring a high wetting of the wall of the dielectric chamber with respect to the conductor liquid 13 surrounds the contact region 15 between the insulating liquid drop 11 and the wall of chamber 12. The surface treatment 14 maintains the positioning of drop 11, preventing the insulating liquid from spreading beyond the desired contact surface. When the system is at rest, the insulating liquid drop 11 naturally takes the shape designated by reference A. "O" designates the axis which is perpendicular to the contact region 15 and passing through the center of contact region 15. At rest, the insulating liquid drop 11 is centered about axis O which constitutes the optical axis of the device. The elements of the device which are adjacent to axis O are transparent. An electrode 16, letting through light in the vicinity of axis O, is placed on the external surface of the wall of dielectric chamber 12, on which is situated the insulating liquid drop 11. An electrode 17 contacts the conductor liquid 13. Electrode 17 may be immersed in liquid 13, or be a conductor deposition achieved on an internal wall of chamber 12.

When a voltage V is established between electrodes 16 and 17, an electrical field is created which, according to the above mentioned electrowetting principle, will increase the wetting of region 15 with respect to conductor liquid 13. As a consequence, conductor liquid 13 moves and deforms the insulating liquid drop 11. A variation of the focus of the lens is thus obtained.

However, the center of the drop is likely to move with respect to axis O during the deformation. Moreover, the outline of the contact surface is likely to lose its circular character during the deformation of the drop. An aspect of the present invention is to maintain the circularity of the drop and its concentricity with respect to axis O while its shape changes by generating an electric field which decreases radially towards the center of region 15.

For avoiding this, according to an aspect of the present invention, a centering means for drop 11 is additionally provided. Examples of such centering means appear in the second to sixth embodiments of the invention described hereinafter.

Figure 2:
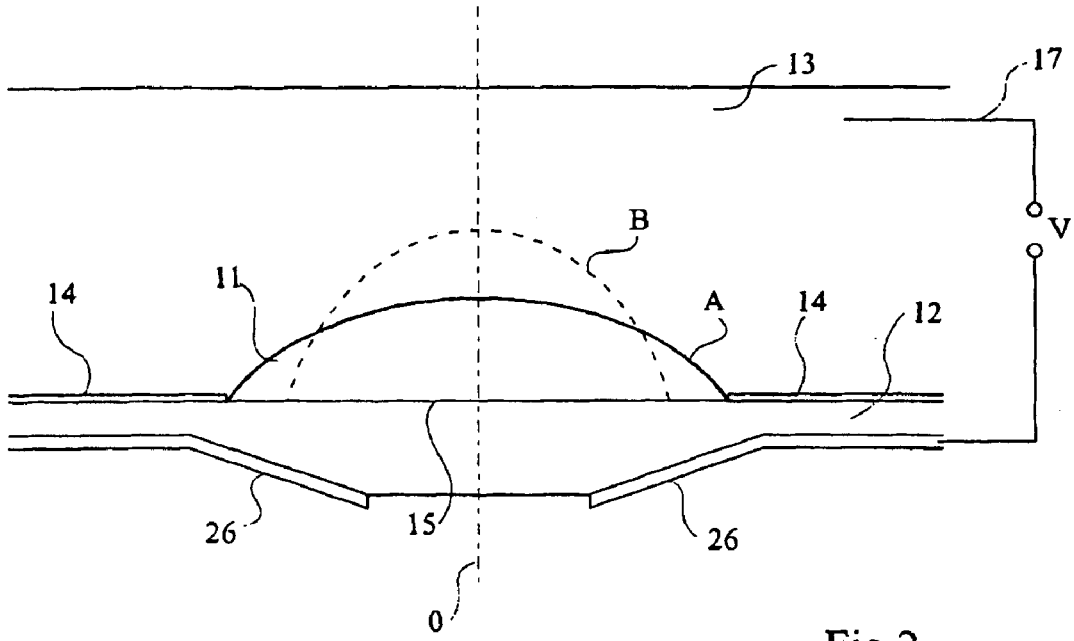
FIG. 2 shows a second embodiment of a variable focus lens according to the present invention.

FIG. 2 shows a simplified cross-section view of a variable focus liquid lens according to a second embodiment of the present invention. Elements such as drop 11, axis O, chamber 12, conductor liquid 13, surface treatment 14, contact region 15 and electrode 17 are the same as those of the embodiment illustrated in FIG. 1. The positions A and B also correspond to the rest position of drop 11 and to the limit position of drop 11, respectively. In this second embodiment, the centering means comprises the generation of an electrical field which decreases radially towards the center of region 15. For this purpose, an electrode 26 is provided which has a surface which progressively departs from the surface of region 15 while approaching axis O. Such an electrode 26 may, for example, be obtained by depositing a metallic film on the lateral walls of a taper centered about axis O, achieved on the external surface of the wall of chamber 12 on which is placed drop 11. An alternative embodiment may consist in depositing a metallic film on the surface of a transparent dielectric resin drop centered about axis O, attached to the external surface of the wall of chamber 12 on which drop 11 is placed. The top of the resin drop is planed in the vicinity of axis O to let the light through.

One may increase voltage V from O volt to a maximum voltage which depends on the used materials. When the maximum voltage is reached, the insulating liquid drop 11 reaches a limit position (designated by reference B). When voltage V varies continuously between O volt and its maximum value, the insulating liquid drop 11 continuously deforms from position A to position B. It will be noted that, drop 11 being of an insulating liquid, no microdroplets are produced at its periphery when the voltage is high, in contrast to what would happen if the drop was of a conductor liquid (see the above mentioned article of Vallet, Berge and Vovelle).

Figure 3:
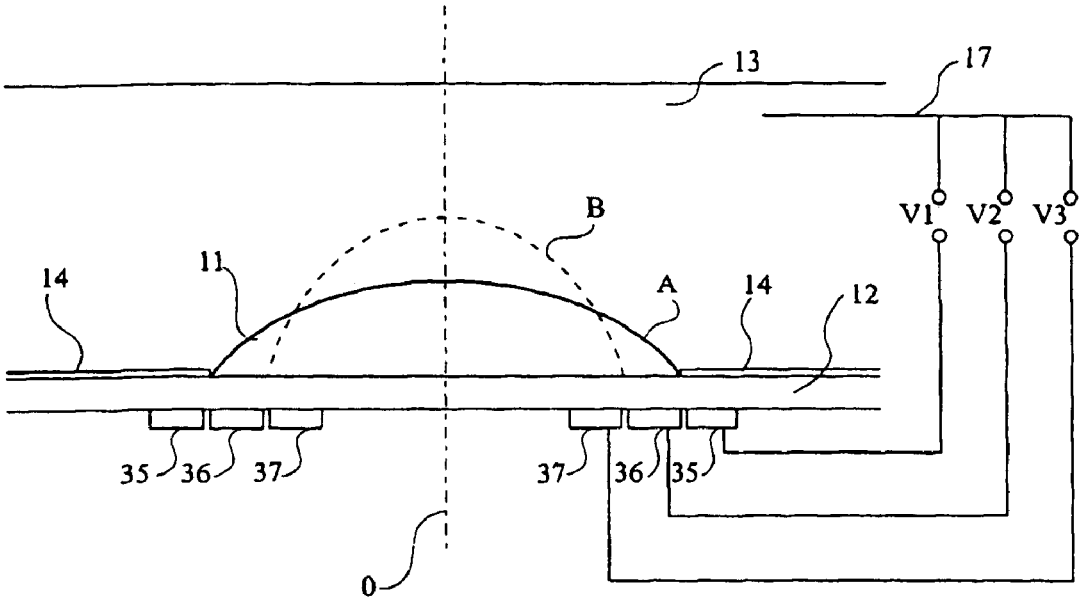
FIG. 3 shows a third embodiment of a variable focus lens according to the present invention.

FIG. 3 shows a simplified cross-section view of a variable focus liquid lens according to a third embodiment of the present invention. Elements such as drop 11, axis O, chamber 12, conductor liquid 13, surface treatment 14, contact region 15 and electrode 17 are the same as those of the embodiment described in FIG. 1. The positions A and B also correspond to the rest position of drop 11 and to the limit position of drop 11, respectively.

In this third embodiment, on the external surface of the wall of chamber 12 is placed a group of three circular concentric electrodes, 35, 36 and 37, insulated from each other, and having O as axis. A voltage may be applied between each of electrodes 35, 36 and 37 and electrode 17; exemplary voltages V1, V2 and V3 are shown, each of which may vary. The voltages are chosen at any time with decreasing values towards axis O so that the electric field generated by applying the voltages to electrodes 35, 36 and 37 decreases radially towards the center of region 15. When voltages V1, V2 and V3 continuously vary between 0 volt and their maximum value, the insulating liquid drop 11 deforms continuously between its rest position A and its limit position B.

According to an alternative of this third embodiment, each electrode 35, 36 and 37 may be connected by a switch, either to a same voltage source V, either to ground. For a constant voltage V, the shape of drop 11 is then varied by varying the number of electrodes to which a voltage is applied. In this case, the focus variation is discrete and not continuous. Only certain predetermined focuses can thus be obtained for the lens comprised of drop 11, but the benefit is then that the voltage control is relatively simple to implement.

Figure 4:
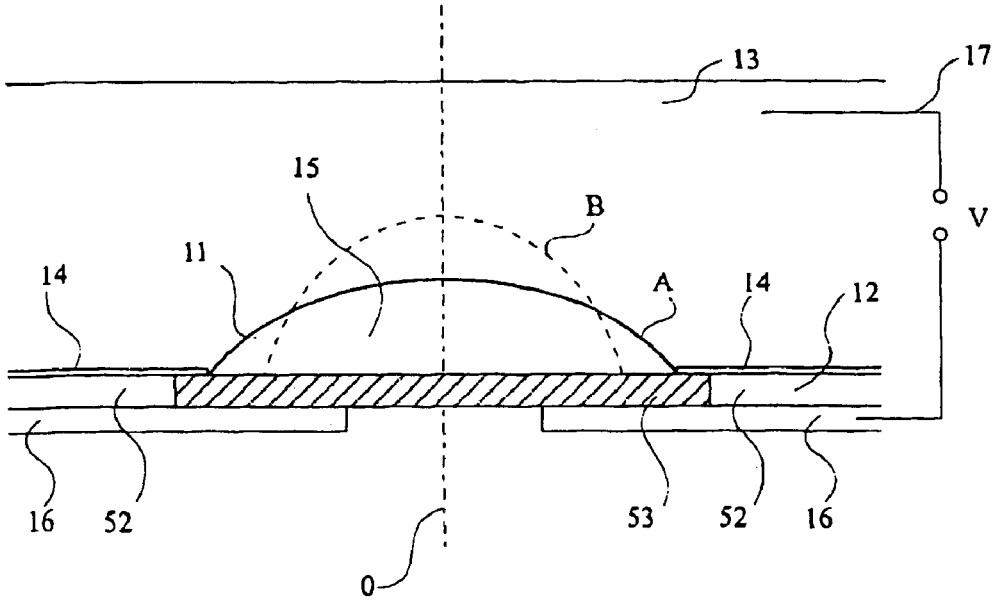
FIG. 4 shows a fourth embodiment of a variable focus lens according to the present invention.

FIG. 4 shows a simplified cross-section view of a variable focus liquid lens according to a fourth embodiment of the present invention. Elements such as drop 11, axis O, conductor liquid 13, surface treatment 14, contact region 15 and electrodes 16 and 17 are the same as those of the embodiment described in FIG. 1. The positions A and B also correspond to the rest position of drop 11 and to the limit position of drop 11, respectively.

In this fourth embodiment, the wall of the dielectric chamber 52 on which the insulating liquid drop 11 is placed, comprises a circular dielectric region 53, letting through the light about axis O. Region 53 has a low wetting with respect to conductor liquid 13 in the absence of a surface treatment 14. Region 53 has been treated in such a way that its dielectric constant varies radially and continuously towards axis O, and that the electric field generated by voltage V has a gradient which decreases radially towards axis O on the contact region 15. When voltage V is varied continuously between 0 volt and its maximum value, the insulating liquid drop 11 continuously deforms between its rest position A and its limit position B.

Figure 5:
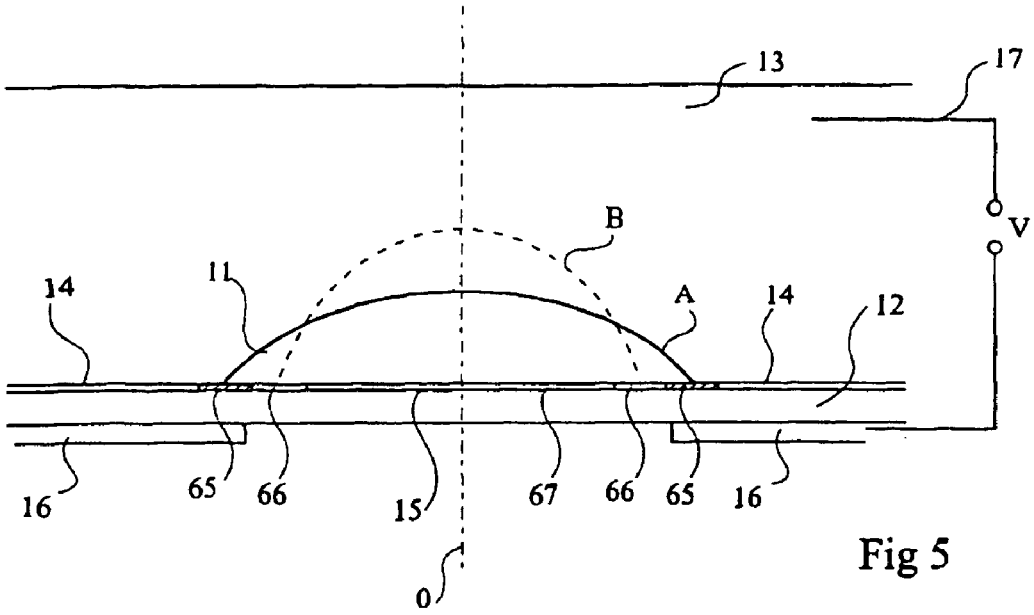
FIG. 5 shows a fifth embodiment of a variable focus lens according to the present invention.

FIG. 5 shows a simplified cross-section view of a variable focus liquid lens according to a fifth embodiment of the present invention. Elements such as drop 11, axis O, dielectric chamber 12, conductor liquid 13, contact region 15 and electrodes 16 and 17 are the same as those of the embodiment described in FIG. 1. The positions A and B also correspond to the rest position of drop 11 and to the limit position of drop 11, respectively.

In this fifth embodiment, the surface of the wall of dielectric chamber 12 on which the insulating liquid drop 11 is placed has been treated at different regions 14, 65, 66 and 67 such that the wetting of regions 14, 65, 66 and 67 with respect to conductor liquid 13 decreases radially towards axis O. A voltage V may be applied between electrode 16 and electrode 17. The electric field generated by voltage V increases the wetting of regions 14, 65, 66 and 67 but maintains the initial wetting gradient. When voltage V varies between 0 volt and its maximum value, the shape of the insulating liquid drop 11 continuously varies between its rest position A and its limit position B.

Figure 6:
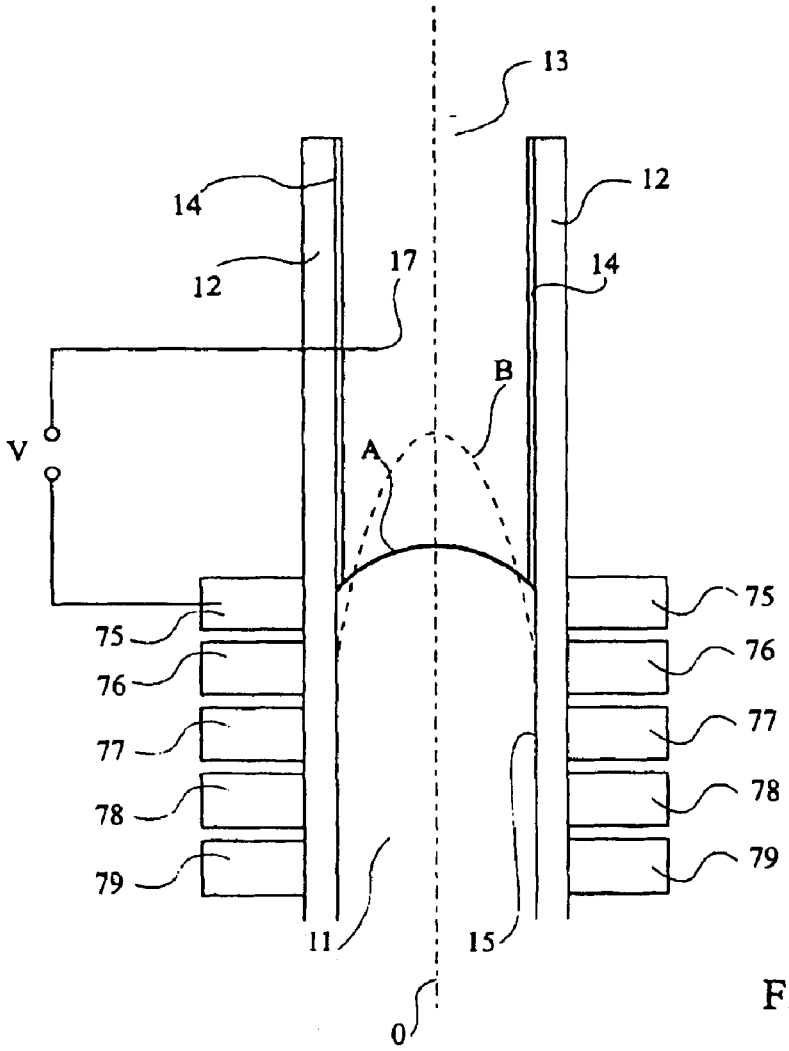
FIG. 6 shows another embodiment of a variable focus lens according to the present invention.

FIG. 6 shows a simplified cross-section view of another embodiment of the present invention in which an insulating liquid 11 occupies the bottom portion of a cylindrical dielectric chamber and is covered by a conductor liquid 13. The chamber is designated by reference 12. The materials composing elements 11, 12 and 13 are the same as those of the previous embodiments.

A surface treatment 14 insuring a high wetting of the internal wall of chamber 12 with respect to the conductor liquid 13 is achieved above the contact region 15 between liquid 11 and the internal surface of chamber 12. The surface treatment 14 allows the position of liquid 11 to be maintained for avoiding this liquid from spreading beyond the contact surface. For simplifying the description only the top portion of liquid 11 will be considered and it will be called, like in the previous embodiment, "drop 11". When the system is at rest, the insulating liquid drop 11 naturally takes the shape designated by reference A. Axis O is the axis of chamber 12. At rest, the insulating liquid drop 11 is centered about axis O which constitutes the optical axis of the device. Several electrodes 75, 76, 77, 78, 79 are placed about the external wall of dielectric chamber 12 in the vicinity of contact region 15. The electrodes 75, 76, 77, 78, 79 are insulated from each other and a voltage V is established between electrode 75 and an electrode 17 contacting the conductor liquid 13. The electrodes 76, 77, 78, 79 are biased through capacitive influence when voltage V is established. At wall 12, the electric field generated by voltage v decreases according to a longitudinal gradient from electrode 75 towards electrode 79. When voltage V increases, conductor liquid 13 moves and deforms the insulating liquid drop 11. A variation of the focus of the lens is thus obtained. The above-mentioned electric field graident insures that the drop permanently has a radial symmetry with respect to axis O. When voltage V varies between 0 volt and its maximum value, the insulating liquid drop 11 varies continuously between its rest position A and its limit position B.

Those skilled in the art will be able to combine the features appearing in the various embodiments of the invention described above.

Moreover, the present invention may be subject to various alternatives which will appear to those skilled in the art.

The surface of the dielectric chamber 12 of FIG. 1 may be concave or convex, in order to obtain a particular diopter value of the device at rest.

The contact region between the insulating liquid drop and the dielectric chamber may be treated for having a high wetting with respect to the insulating liquid, in order to simplify the positioning of the insulating liquid drop.

In the case of a dielectric chamber naturally having a high wetting with respect to the conductor liquid, the contact region may be achieved by a surface treatment adapted to providing it with a low wetting with respect to the conductor liquid.

The surface treatment 14 may consist of depositing or sticking a film of a material having a high wetting with respect to conductor liquid 13.

Electrode 16 of FIG. 1 may be replaced with a conductor liquid in contact with the external surface of chamber 12, voltage V then being established between this conductor liquid and liquid 13.

It will be possible to realize a device including an array formed of groups of three, separately controlled, variable focus lenses, colored in red, green, and blue, operating, for example, in a binary mode, stopping or allowing through light originating from a unique source of white light, thus forming a luminous color screen which may be of big size and of moderate cost.

It will be possible to realize a device in which the above mentioned centering means are no longer used for maintaining drop 11 circular throughout its deformation, but in contrast for making the drop go from a rest position determined, for example, by the shape of the surface treatment 14, to an operating shape, determined, for example, by the outline of electrode 16. It is thus possible to create a variable focus cylindrical lens by using a surface treatment 14 of rectangular shape and centering electrodes 16 of rectangular outline.

It will be possible to apply the present invention to a device bridging more than one wall of chamber 12, drop 11 being placed, for example, in an angle or in a corner of chamber 12. According to this alternative, an electrode would of course be placed on the back surface of each wall in contact with drop 11, at the level of the contact region. Such an alternative would enable a variable deflection prism to be achieved.

As an example of conductor liquid 13, one may use water loaded with salts (mineral or other) or any other liquid, organic or not, which is conductive or made conductive by addition of ionic components. As an insulating liquid 11, one may use oil, an alcane or a blend of alcanes, eventually halogenated, or any other insulating liquid which is not miscible with conductor liquid 13. Chamber 12 may be comprised of a glass plate, treated with silane or covered with a thin coating of fluorinated polymer or of a sandwich of fluorinated polymer, epoxy resin, polyethylene.

Voltage V will preferably be alternating in order to avoid the accumulation of electric charges throughout material 12 from the surface on which drop 11 is placed.

In the exemplary embodiment of FIG. 1, drop 11 has a rest diameter of approximately 6 mm. The conductor liquid 13 and the insulating liquid of drop 11 being substantially of same density, drop 12 has a hemispheric shape. When it is at rest (position A), the edge of drop 11 is at an angle of approximately 45° to the surface of chamber 12. In its limit position (position B), the edge of drop 11 is at an angle of approximately 90° to the surface of chamber 12. The described device, using as a conductor liquid 13 salt water of optical index 1.35 and, for the insulating liquid of drop 11, oil having an optical index of 1.45, achieves approximately 40 diopters of focus variation for an applied voltage of 250 volts and an electrical power of some mW. The frequency of the alternating voltage is in this case comprised between 50 and 10,000 Hz, its period being substantially smaller than the response time of the system which is several hundredths of a second.

The variable focus lens according to the present invention may have a size comprised between several tens of μm and several tens of mm, and may in particular be applied to the field of optoelectronic systems or to endoscopy.

What is claimed is:

1. A variable focus lens comprising a chamber (12) filled with a first liquid (13), a drop of a second liquid (11) being disposed at rest on a region of a first surface of an insulating wall of the chamber, the first and second liquids being non miscible, of different optical indexes and of substantially same density, characterized in that:

the first liquid is conductive;

the second liquid is insulating;

in that it comprises:

means for applying a voltage between the conductor liquid and an electrode (16; 26; 35–37; 75–79) placed on the second surface of said wall; and centering means for maintaining the centering of the edge of the drop while the voltage is applied and for controlling the shape thereof.

2. The variable focus lens according to claim 1, in which the centering means allows a continuous maintaining of the centering of the drop and a continuous control of the shape of the edge of the drop while a varying voltage is applied by said means for applying a voltage.

3. The variable focus lens according to claim 2, in which the first surface is substantially flat, the contact region (15) is circular and centered about an axis (O) which is perpendicular to the first surface.

4. The variable focus lens according to claim 3, in which the centering means corresponds to a progressive thickening of the second surface of the wall of the chamber towards said axis, said electrode (26) being applied against said second surface.

5. The variable focus lens according to claim 3, in which the centering means corresponds to a radial decrease of the wetting with respect to the first liquid (13), towards the center of said contact region (15) with the second liquid.

6. The variable focus lens according to claim 3, in which the centering means corresponds to a radial gradient of the dielectric constant of said wall of the chamber (53) at the level of said contact region (15) with the second liquid.

7. The variable focus lens according to claim 1, in which the first surface is substantially flat, the contact region (15) is circular and centered about an axis (O) perpendicular to the first surface, and wherein the centering means comprises an electrode formed of one or several circular concentric strips (35–37) insulated from each other, centered about said axis, the circular strips being supplied by distinct voltage sources of values decreasing towards said axis.

8. The variable focus lens according to claim 1, in which the chamber is cylindrical, the first surface is the internal surface of the chamber, the contact region with the second liquid corresponds to a cylindrical section of the chamber, the centering means is comprised of one or several cylindrical electrodes of same diameter, insulated from each other, placed side by side against the external surface of the chamber at the level of the border of said contact region, the electrodes being supplied by different voltage of values decreasing towards the center of said contact region.

9. The variable focus lens according to claim 1, in which the first surface is substantially flat, the contact region (15) is rectangular and symmetric with respect to an axis (O) perpendicular to the first surface and the centering means is comprised of an electrode formed of one or several rectangular concentric strips insulated from each other, symmetric with respect to said axis (O), the rectangular strips being supplied by distinct voltage sources of decreasing values towards said axis.

10. The variable focus lens according to claim 1, in which said wall is comprised of two non parallel planes and in which said region bridges said two planes.

*11. A variable focus lens comprising:*

*a chamber containing a first liquid, the first liquid being conductive;*

*a drop of a second liquid being disposed on a contact region of a first surface of an insulating wall of the chamber, the second liquid being insulating, the first and second liquids being non miscible, of different optical indexes and of substantially same density;*

*a voltage source configured for applying a voltage between the first liquid and an electrode placed on a second surface of said wall; and*

*centering means for maintaining the centering of the edge of the drop while the voltage is applied and for controlling the shape thereof.*

*12. The variable focus lens according to claim 11, in which the centering means allows a continuous maintaining of the centering of the drop and a continuous control of the shape of the edge of the drop while a varying voltage is applied by said voltage source.*

*13. The variable focus lens according to claim 12, in which the first surface is substantially flat, the contact region is circular and centered about an axis which is perpendicular to the first surface.*

*14. The variable focus lens according to claim 13, in which the centering means corresponds to a progressive thickening of the second surface of the wall of the chamber towards said axis, said electrode being applied against said second surface.*

*15. The variable focus lens according to claim 13, in which the centering means corresponds to a radial decrease of the wetting with respect to the first liquid, towards the center of said contact region with the second liquid.*

*16. The variable focus lens according to claim 13, in which the centering means corresponds to a radial gradient of the dielectric constant of said wall of the chamber at the level of said contact region with the second liquid.*

*17. The variable focus lens according to claim 11, in which the first surface is substantially flat, the contact region is circular and centered about an axis perpendicular to the first surface, and wherein the centering means comprises an electrode formed of one or several circular concentric strips insulated from each other, centered about said axis, the circular strips being supplied by distinct voltage sources of values decreasing towards said axis.*

*18. The variable focus lens according to claim 11, in which the chamber is cylindrical, the first surface is the internal surface of the chamber, the contact region with the second liquid corresponds to a cylindrical section of the chamber, and the centering means comprises:*

*one or more cylindrical electrodes of same diameter, insulated from each other, placed side by side against an external surface of the chamber at the level of the border of said contact region, the electrodes being supplied by different voltages of values decreasing towards the center of said contact region.*

*19. The variable focus lens according to claim 11, in which the first surface is substantially flat, the contact region is rectangular and symmetric with respect to an axis perpendicular to the first surface, and the centering means comprises:*

*an electrode formed of one or more rectangular concentric strips insulated from each other, symmetric with respect to said axis, the rectangular strips being supplied by distinct voltage sources of decreasing values towards said axis.*

*20. The variable focus lens according to claim 11, in which said wall is comprised of two non parallel planes and in which said contact region bridges said two planes.*

*21. The variable focus lens according to claim 14, wherein the progressive thickening of the second surface comprises a dielectric drop centered about said axis.*

*22. The variable focus lens according to claim 11, in which the first surface is substantially flat, the contact region is circular and centered about an axis perpendicular to the first surface, and wherein the centering means comprises an electrode formed of circular concentric strips insulated from each other, centered about said axis, the concentric strips being connected to each other via switches configured to vary the number of concentric strips to which a voltage is applied to vary the shape of the drop.*

*23. The variable focus lens according to claim 11, wherein the first surface has one of a concave and a convex shape.*

*24. The variable focus lens according to claim 11, wherein the contact region has a high wetting with respect to the drop.*

*25. The variable focus lens according to claim 11, wherein the contact region has a low wetting with respect to the first liquid, and a region of the first surface surrounding the contact region has a high wetting with respect to the first liquid.*

*26. A variable focus lens comprising:*

*a chamber containing a first liquid, the first liquid being conductive;*

*a drop of a second liquid being disposed on a contact region of a first surface of an insulating wall of the chamber, the second liquid being insulating, the first and second liquids being non miscible, of different optical indexes and of substantially same density;*

*a voltage source configured for applying a voltage between the first liquid and a second conducting liquid contacting a second surface of said wall; and*

*centering means for maintaining the centering of the edge of the drop while the voltage is applied and for controlling the shape thereof.*

*27. An array of variable focus lenses, each of the lenses in the array comprising:*

*a chamber containing a first liquid, the first liquid being conductive;*

*a drop of a second liquid being disposed on a contact region of a first surface of an insulating wall of the chamber, the second liquid being insulating, the first and second liquids being non miscible, of different optical indexes and of substantially same density;*

*a voltage source configured for applying a voltage between the first liquid and an electrode placed on a second surface of said wall; and*

*centering means for maintaining the centering of the edge of the drop while the voltage is applied and for controlling the shape thereof.*

*28. The array of variable focus lenses according to claim 27, wherein the lenses are arranged in groups of three.*

*29. The array of variable focus lenses according to claim 28, wherein the groups of three comprises lenses colored in red, blue and green.*

*30. The array of variable focus lenses according to claim 27, wherein the lenses are arranged to form part of a color screen.*

*31. The variable focus lens according to claim 11, wherein the first liquid comprises water loaded with salts.*

*32. The variable focus lens according to claim 11, wherein the second liquid comprises at least one of an oil, an alkane, and a blend of alkanes.*

*33. The variable focus lens according to claim 11, wherein the insulating wall comprises a glass plate treated with silane.*

*34. The variable focus lens according to claim 11, wherein the insulating wall comprises a glass plate coated with a coating comprising fluorinated polymer.*

*35. The variable focus lens according to claim 34, wherein the insulating wall comprises a glass plate coated with a coating comprising a sandwich of fluorinated polymer, epoxy resin and polyethylene.*

*36. The variable focus lens according to claim 11, wherein the drop has a rest diameter of about 6 mm.*

*37. A variable focus lens comprising:*

*a liquid containment structure having a wall made of insulating material;*

*a first, conductive liquid contained in the liquid containment structure and being in contact with the wall;*

*a drop of a second, insulating liquid being disposed on a contact region of a first insulating surface of the wall of the liquid containment structure, the first and second liquids being non miscible and of different optical indexes;*

*an electrode insulated from the first liquid and positioned in the vicinity where the first liquid is in contact with the wall; and*

*a voltage source configured for creating an electric field between the first liquid and the electrode.*

*38. A variable focus lens according to claim 37, wherein the wall of the liquid containment structure comprises a flat wall member.*

*39. A variable focus lens according to claim 37, wherein the wall of the liquid containment structure comprises a cylindrical wall section.*

*40. A variable focus lens according to claim 39, wherein the electrode comprises at least one cylindrical electrode surrounding the cylindrical wall section.*

*41. A variable focus lens according to claim 37, wherein the first and second liquids have substantially the same density.*

*42. A variable focus lens according to claim 37, further comprising a centering means for maintaining the centering of the drop about its optical axis and for controlling the shape of the drop while the voltage is applied.*

*43. A variable focus lens according to claim 42, wherein the centering means comprises a cylindrical wall section containing the drop.*

*44. A variable focus lens comprising:*

*a chamber having a wall of insulating material;*

*a first liquid being disposed within the chamber and contacting the wall of the chamber, the first liquid being conducting;*

*a second liquid being disposed within the chamber and having an interface with the first liquid, the second liquid being insulating, the first and second liquids being non miscible;*

*an electrode positioned on the opposite side of the wall with respect to the first liquid; and*

*a voltage source configured for applying a voltage between the first liquid and the electrode so as to change the wetability between the first liquid and the wall and thereby change the shape of the interface between the first liquid and the second liquid.*

*45. A variable focus lens according to claim 44, wherein the chamber wall comprises a cylindrical wall section.*

*46. A variable focus lens according to claim 44, wherein the first and second liquids have substantially the same density.*

*47. A method of forming a lens of a variable focus lens, comprising:*

*providing a chamber containing a first liquid and a second liquid, the first liquid being conductive and contacting a wall of the chamber, the second liquid having an interface with the first liquid, the second liquid being insulating, the first and second liquids being non miscible, the wall being insulating; and*

*providing a voltage source for applying a voltage between the first liquid and an electrode so as to increase the wetting between the first liquid and the wall and thereby change the shape of the interface between the first liquid and the second liquid.*

*48. A method of forming a lens of a variable focus lens, comprising:*

*providing a chamber containing a first liquid and a second liquid, the first liquid being conductive and contacting a wall of the chamber, the second liquid having an interface with the first liquid, the second liquid being insulating, the first and second liquids being non miscible; and*

*providing a plurality of distinctive voltage sources for applying a plurality of distinctive voltages between the first liquid and an electrode to thereby change the shape of the interface between the first liquid and the second liquid.*

*49. The method of forming a lens of a variable focus lens according to claim 48, wherein at least one of the plurality of the voltage sources comprises an alternating voltage source.*

*50. The method of forming a lens of a variable focus lens according to claim 48, wherein at least one of the plurality of the voltage sources comprises an alternating voltage source having a frequency range between 50 and 10,000 Hz.*

*51. The method of forming a lens of a variable focus lens according to claim 48, wherein the first and second liquids have substantially the same density.*

*52. A method of forming a lens of a variable focus lens, comprising:*

*providing a chamber containing a first liquid and a drop of a second liquid, the first liquid being conductive, the second liquid having an interface with the first liquid, the second liquid being insulating, the first and second liquids being non miscible, and of different optical indexes; and*

*providing a voltage source for varying a voltage so as to maintain the centering of the drop and to continuously control the shape of the edge of the drop.*

*53. A method of forming a lens of a variable focus lens, comprising:*

*providing a chamber containing a first liquid and a drop of a second liquid, the first liquid being conductive, the second liquid having an interface with the first liquid, the second liquid being insulating, the first and second liquids being non miscible, and of different optical indexes; and*

*providing a voltage source capable of applying a voltage so that the electric field decreases radially toward a center of a contact region upon which the drop is disposed.*

*54. A method of forming a lens of a variable focus lens, comprising:*

*providing a chamber containing a first liquid and a drop of a second liquid, the first liquid being conductive, the second liquid having an interface with the first liquid, the second liquid being insulating, the first and second liquids being non miscible, and of different optical indexes; and*

*providing a voltage source capable of controlling the shape of the edge of the drop by varying the number of electrodes to which a voltage is applied.*

*55. A method of changing the focus of a variable focus lens of the type comprising a liquid containment structure having a wall of insulating material, a body of a first, conductive liquid in contact with the wall, a drop of a second, insulating liquid in contact with the first liquid to form an interface therebetween, wherein the first and second liquids are non miscible and have different optical indexes, and a voltage source, the method comprising:*

*selectively applying a voltage differential between the first liquid and the wall sufficient to change the wetability of the first liquid with respect to the wall to change the shape of the body of the first liquid; and*

*using the change in the shape of the body of first liquid to change the shape of the interface between the first and second liquids.*

*56. A method of changing the focus of a variable focus lens according to claim 55, wherein the liquid containment structure comprises a cylindrical wall section.*

*57. A method of changing the focus of a variable focus lens according to claim 55, wherein the first and second liquids have substantially the same density.*

*58. A method of changing the focus of a variable focus lens, comprising:*

*selectively applying a voltage across a body of a first, conductive liquid sufficient to change the shape of the body of the first liquid; and*

*using the change in the shape of the body of first liquid to change the shape of an interface between the first liquid and a drop of a second, insulating liquid in contact with the first liquid to form the interface therebetween, wherein the first and second liquids are non miscible and have different optical indexes.*

*59. A method of changing the focus of a variable focus lens according to claim 58, wherein the first and second liquids have substantially the same density.*

* * * * *